US010964011B2

(12) United States Patent
Cosatto et al.

(10) Patent No.: US 10,964,011 B2
(45) Date of Patent: Mar. 30, 2021

(54) ANOMALY DETECTION WITH PREDICTIVE NORMALIZATION

(71) Applicant: NEC Laboratories America, Inc., Princeton, NJ (US)

(72) Inventors: Eric Cosatto, Red Bank, NJ (US); Felix Wu, Ithaca, NY (US); Alexandru Niculescu-Mizil, Plainsboro, NJ (US)

(73) Assignee: NEC Corporation (JP)

( * ) Notice: Subject to any disclaimer, the term of this patent is extended or adjusted under 35 U.S.C. 154(b) by 0 days.

(21) Appl. No.: 16/703,349

(22) Filed: Dec. 4, 2019

(65) Prior Publication Data
US 2020/0111204 A1 Apr. 9, 2020

Related U.S. Application Data

(63) Continuation-in-part of application No. 15/983,342, filed on May 18, 2018, now Pat. No. 10,733,722.
(60) Provisional application No. 62/525,291, filed on Jun. 27, 2017, provisional application No. 62/779,562, filed on Dec. 14, 2018.

(51) Int. Cl.
  *G06T 7/00* (2017.01)
  *G06K 9/62* (2006.01)
  *G06N 3/08* (2006.01)
  *G06N 3/04* (2006.01)
(52) U.S. Cl.
  CPC .......... *G06T 7/0004* (2013.01); *G06K 9/6228* (2013.01); *G06K 9/6256* (2013.01); *G06K 9/6267* (2013.01); *G06N 3/04* (2013.01); *G06N 3/084* (2013.01); *G06N 3/088* (2013.01);
(Continued)

(58) Field of Classification Search
  CPC .... G06T 7/004; G06K 9/6228; G06K 9/6256; G06K 9/6267; G06N 3/04; G06N 3/084; G06N 3/088
  See application file for complete search history.

(56) References Cited

U.S. PATENT DOCUMENTS

2017/0076224 A1\* 3/2017 Munawar ............... G06N 3/084

OTHER PUBLICATIONS

Pathak et al., "Context Encoders: Feature Learning by Inpainting", arXiv:1604.07379v2 [cs.CV] Nov. 21, 2016, pp. 1-12.
(Continued)

*Primary Examiner* — Leon Flores
(74) *Attorney, Agent, or Firm* — Joseph Kolodka

(57) ABSTRACT

A method is provided for model training to detect defective products. The method includes sampling training images of a product to (i) extract image portions therefrom made of a center patch and its context and (ii) black-out the center patch. The method further includes performing unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model. The method also includes sampling positive and negative center-patch-sized portions from the training images. The method additionally includes normalizing, using the trained CAE model, the positive and negative center-patch-sized portions. The method further includes performing supervised training of a classifier model using the normalized positive and negative center-patch-sized portions to obtain a trained supervised classifier model for detecting the defective products.

11 Claims, 12 Drawing Sheets

(52) U.S. Cl.
CPC .............. *G06T 2207/20081* (2013.01); *G06T 2207/20084* (2013.01)

(56) References Cited

OTHER PUBLICATIONS

Yeh et al., "Semantic Image Inpainting with Deep Generative Models", arXiv:1607.07539v3 [cs.CV] Jul. 13, 2017, pp. 1-19.
Van den Oord et al., "Conditional Image Generation with PixelCNN Decoders", 30th Conference on Neural Information Processing Systems (NIPS 2016), Dec. 2016, pp. 1-9.
Sakurada et al., "Anomaly Detection Using Autoencoders with Nonlinear Dimensionality Reduction", MLSDA '14, Dec. 2014, pp. 1-8.
An, "Variational Autoencoder Based Anomaly Detection Using Reconstruction Probability", Special Lecture on IE, Dec. 2015, pp. 1-18.
Schlegl, "Unsupervised Anomaly Detection with Generative Adversarial Networks to Guide Marker Discovery", IPMI, Mar. 2017, pp. 1-12.

\* cited by examiner

ANOMALY DETECTION WITH PREDICTIVE NORMALIZATION

RELATED APPLICATION INFORMATION

This application claims priority to the U.S. Provisional application No. 62/779,562 filed on Dec. 14, 2018, incorporated herein by reference in its entirety. This application is also a Continuation-in-Part of U.S. Non-Provisional application Ser. No. 15/983,342 filed on May 18, 2018, entitled "RECONSTRUCTOR AND CONTRASTOR FOR ANOMALY DETECTION", incorporated herein by reference in its entirety. This application is also related to U.S. Non-Provisional application Ser. No. 15/983,392 filed on May 18, 2018, entitled "RECONSTRUCTOR AND CONTRASTOR FOR MEDICAL ANOMALY DETECTION", incorporated herein by reference in its entirety, and U.S. Provisional Application No. 62/525,291 filed on Jun. 27, 2017 incorporated herein by reference in its entirety.

BACKGROUND

Technical Field

The present invention relates to anomaly detection and more particularly to anomaly detection with predictive normalization.

Description of the Related Art

Detecting small and faint anomalies is a difficult problem for a human and one that benefits greatly from automation. For example, x-ray images of metallic objects may reveal tiny hidden micro-fractures that have very low contrast with the surrounding pixel intensities. Detection of such anomalies is difficult for humans and automated systems. Increasing the accuracy of such detection is very valuable for quality assurance and quality control.

SUMMARY

According to an aspect of the present invention, a computer-implemented method is provided for model training to detect defective products. The method includes sampling, by a hardware processor, training images of a product to (i) extract image portions therefrom made of a center patch and its context and (ii) black-out the center patch. The method further includes performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model. The method also includes sampling, by the hardware processor, positive and negative center-patch-sized portions from the training images. The method additionally includes normalizing, by the hardware processor using the trained CAE model, the positive and negative center-patch-sized portions. The method further includes performing, by the hardware processor, supervised training of a classifier model using the normalized positive and negative center-patch-sized portions to obtain a trained supervised classifier model for detecting the defective products.

According to another aspect of the present invention, a computer program product is provided for model training to detect defective products. The computer program product includes a non-transitory computer readable storage medium having program instructions embodied therewith. The program instructions are executable by a computer to cause the computer to perform a method. The method includes sampling, by a hardware processor of the computer, training images of a product to (i) extract image portions therefrom made of a center patch and its context and (ii) black-out the center patch. The method further includes performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model. The method also includes sampling, by the hardware processor, positive and negative center-patch-sized portions from the training images. The method additionally includes normalizing, by the hardware processor using the trained CAE model, the positive and negative center-patch-sized portions. The method further includes performing, by the hardware processor, supervised training of a classifier model using the normalized positive and negative center-patch-sized portions to obtain a trained supervised classifier model for detecting the defective products.

According to yet another aspect of the present invention, a computer processing system is provided for model training to detect defective products. The computer processing system includes a memory device including program code stored thereon. The computer processing system further includes a hardware processor, operatively coupled to the memory device, and configured to run the program code stored on the memory device to sample training images of a product to (i) extract image portions therefrom made of a center patch and its context and (ii) black-out the center patch. The processor is further configured to run the program code to perform unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model. The processor is also configured to run the program code to sample positive and negative center-patch-sized portions from the training images. The processor is additionally configured to run the program code to normalize, using the trained CAE model, the positive and negative center-patch-sized portions. The processor is further configured to run the program code to perform supervised training of a classifier model using the normalized positive and negative center-patch-sized portions to obtain a trained supervised classifier model for detecting the defective products.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
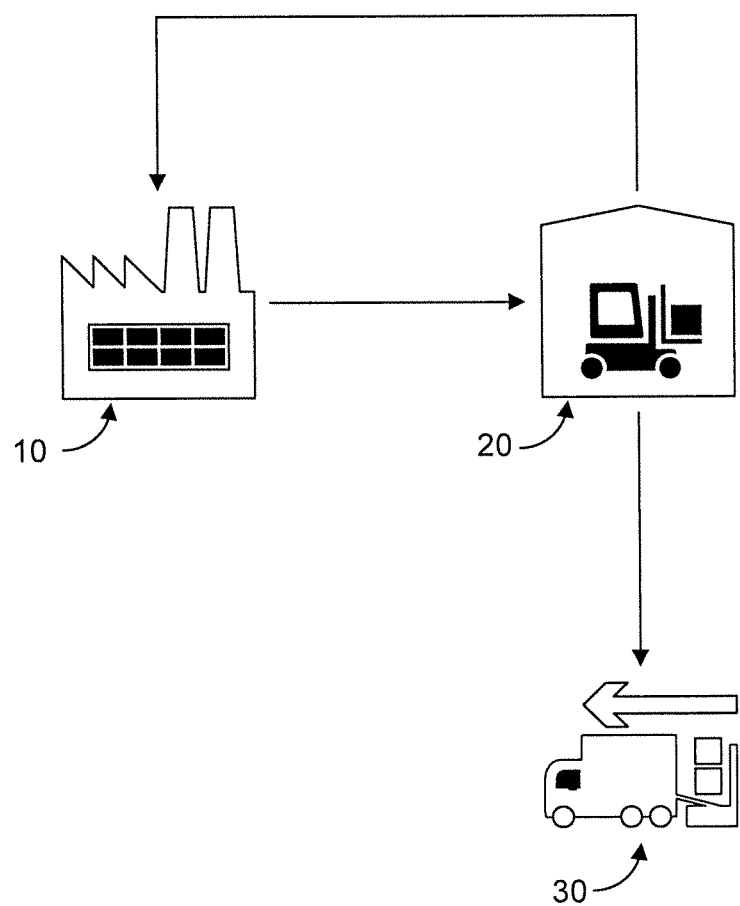
FIG. 1 is a block/flow diagram illustrating a high-level system/method for correcting defective products, in accordance with the present principles.

In accordance with the present principles, systems and methods are provided for anomaly detection with predictive normalization. In particularly useful embodiments, systems and methods can be configured to correct defects in products, such as, e.g., manufactured products.

In one embodiment, a product is inspected for defects using a reconstructor and contrastor. The reconstructor can include an encoder-decoder arrangement employed to reconstruct images of a product containing defects. The encoder-decoder arrangement is trained from examples that contain no defects. Thus, the encoder-decoder arrangement will use an incomplete image of the product, and reconstruct the image according to the defectless training. As a result, a reconstructed image of the product can be produced where the reconstructed image depicts the product having no defects.

The contrastor can then determine a difference between the reconstructed image and an original image of the product. If there is a substantial difference between the original image and the reconstructed image, then the product is considered not defectless. In other words, by failing to match a defectless reconstructed image of the product, it can be determined that the product does contain some anomaly or defect.

Because the systems and methods employed determine if a product fails to match a defectless reconstruction, an encoder-decoder arrangement can be trained with only normal, defectless images of the product. Thus, training samples can be found in abundance, and thus training the encoder-decoder arrangement can be cheap and efficient.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now in detail to the figures in which like numerals represent the same or similar elements and initially to FIG. 1, a high-level system/method for correcting defective products is illustratively depicted in accordance with one embodiment of the present principles.

In one embodiment, a manufacturing plant 10 manufactures products. The manufactured products may be any physical product. The manufactured products can sometimes be manufactured with defects. Thus, the manufactured products can be sent to a quality assurance system 20.

The quality assurance system 20 inspects the manufactured products to ensure that the products live up to quality standards with respect to issues such as defects and anomalies in the products. Such defects can include visual defects, such as, e.g., cracks, holes, protrusions, discolorations, or any feature that is not part of the original design of the product. The quality assurance system 20 can include an automated system for performing the inspections, such as, e.g., an automated visual system including a camera. However, other inspection systems can be used, including, e.g., radar, infrared, ultrasound, or other detection methods. Based on results, the quality assurance system 20 can automatically take steps to correct the product defects. Such steps can include, e.g., discarding the defecting product, automatically listing the product as defective and requiring refurbishment, alerting an operator to the defect, or any other corrective action.

According to an aspect of the present invention, the corrective action can include listing the product as defective and sending the product back to the manufacturing plant 10 to be recycled or refurbished. However, if the product is not defective, the product can be forwarded to a shipping and packaging system 30 to be sent to a customer.

Figure 2:
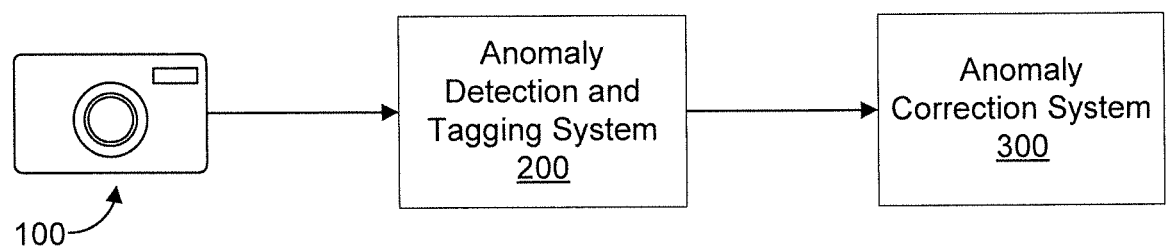
FIG. 2 is a block/flow diagram illustrating a system/method for detecting and correcting defects and anomalies, in accordance with the present principles.

Referring now to FIG. 2, a system/method for detecting and correcting defects and anomalies is illustratively depicted in accordance with an embodiment of the present principles.

According to aspects of the present invention, defects and anomalies in an item are captured by an imaging device 100. The imaging device 100 captures images of an item for analysis to facilitate recognizing defects and anomalies. For example, the imaging device 100 can include, e.g., a camera device or multiple camera devices for capturing images of either the entire item or a portion of the item. Accordingly, multiple imaging devices 100 can be used to concurrently capture images of the item from multiple perspectives. Thus, the entirety of the item, such as, e.g., an entire surface, or for suitable imaging devices 100, an entirety of the depth (as can be the case for imaging devices 100 including, e.g., magnetic resonance imaging (MRI) or computer aided tomography, etc.) can be captured by the imaging device 100. Alternatively, a single imaging device 100 can be used, and the item and the imaging device 100 can be moved relative to each other to capture images from multiple perspectives by, e.g., conveyor, gimbal, or moving stage. The imaging device 100 can also include, e.g., an infrared sensor, a radar sensor, an ultrasound sensor, a light detection and ranging (LIDAR) sensor, among others. Thus, the imaging device 100 can generate an image of the item for analysis.

The image can then be analyzed by an anomaly detection and tagging system 200. The anomaly detection and tagging system 200 process the image to recognize the presence of any potential anomalies with the item according to the image from the imaging device 100. Here, an anomaly is considered to be a feature of the item, as depicted in the image, that deviates from what is usually present at that location of the item. For example, the anomaly detection and tagging system 200 can compare the image of the item to defectless items. Therefore, when the anomaly detection and tagging system 200 analyzes an image of an item that is different from the a defectless item, the anomaly detection and tagging system 200 will determine where in the image and on the item the difference is from the defectless item. The anomaly detection and tagging system 200 can then tag the feature of the item that is different from the defectless item as a potential anomaly or defect.

Information regarding the tagged anomaly can then be provided to an anomaly correction system 300 to take corrective action. The corrective action can depend on the severity of the defects. For example, if the item is a manufactured product, the production line may be stopped, or the item may be discarded or otherwise removed for recycling or refurbishment. A threshold may be used as well, such that if a threshold number of anomalies are tagged, more drastic action may be taken. For example, if the item is a manufactured product, reaching a first threshold number of anomalies can result in the item being discarded, while reaching a second threshold can result in a halting of the entire production line. Alternatively, or in addition, the anomaly correction system 300 can include a notification device to notify an operator of the item having tagged anomalies.

Figure 3:
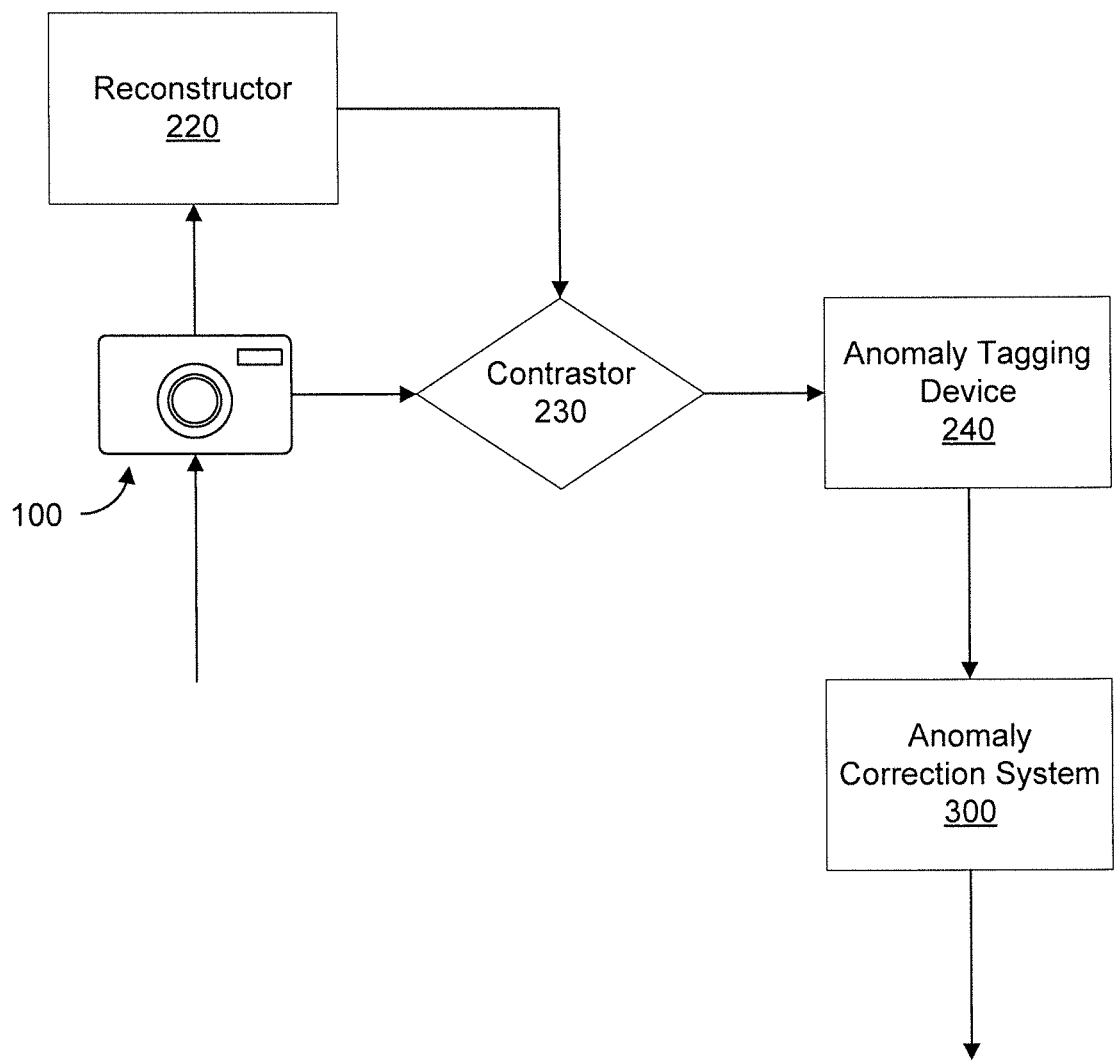
FIG. 3 is a block/flow diagram illustrating a system/method for detecting and correcting defects and anomalies using a reconstructor and contrastor, in accordance with the present principles.

Referring now to FIG. 3, a system/method for detecting and correcting defects and anomalies using a reconstructor and contrastor is illustratively depicted in accordance with the present principles.

According to aspects of the present invention, an image of an item taken by an imaging device 100 can be provided to both a reconstructor 220 and a contrastor 230. The reconstructor 220 can receive the image of the item, e.g., in a memory or storage, and generate a reconstructed image of the item that does not include any defects or anomalies such that the reconstructed image can be contrasted with the original image at the contrastor 230.

The reconstructor 220 will receive the image of the item and reconstruct the image to remove any defects or anomalies. For example, the reconstructor can divide the image in multiple smaller portions of the image, partially mask a region in each smaller portion, and reconstruct each portion. However, other methods of reconstructing the image are contemplated. The reconstructor 220 can include, e.g., a processor to perform reconstruction on the image stored in a memory, such as, e.g., a storage, a random access memory (RAM), a buffer, or a cache, among others. The reconstructor 220 will, therefore, generate with the reconstructed image, a representation of the item that has no defects or anomalies. The reconstructed image can be stored or cached in a storage device, such as, e.g. a RAM, a buffer or a cache.

The reconstructed image will then be provided to the contrastor 230 along with the original image from the imaging device 100. The contrastor 230 can then compare the reconstructed image with the original image. Because the reconstructed image is a defectless representation of the item, any differences between the reconstructed image and the original image will be detected by the contrastor 230. Similar to the reconstructor 220, the contrastor 230 can include, e.g., a processor, to perform the contrasting, and a storage, such as, e.g., a RAM, buffer or cache, to temporarily or permanently store the original image and the reconstructed image.

The contrastor 230 will then provide data regarding the detected difference to an anomaly tagging device 240. The anomaly tagging device 240 will use data regarding the locations of difference between the reconstructed image and the original image to identify anomalies. Thus, the anomaly tagging device 240 can generate a tagged image of the item with anomalies identified and tagged.

The tagged image can be used by the anomaly correction system 300 to take corrective action regarding the anomalies, as described above. For example, the anomaly correction system 300 can, e.g., automatically determine that an item should be discarded if it has a certain number of anomalies. Alternatively, the anomaly correction system 300 can automatically determine that an item should be discarded if it has any anomalies, or that the item can be sent back to manufacturing to be refurbished or recycled. The anomaly correction system 300 can even, e.g., automatically determine that an entire production line should be stopped if an item with anomalies is found, or if a certain number of items with anomalies is found. The anomaly correction system 300 can also, e.g., notify an operator of the anomalies and providing the operator with the tagged image.

Figure 4:
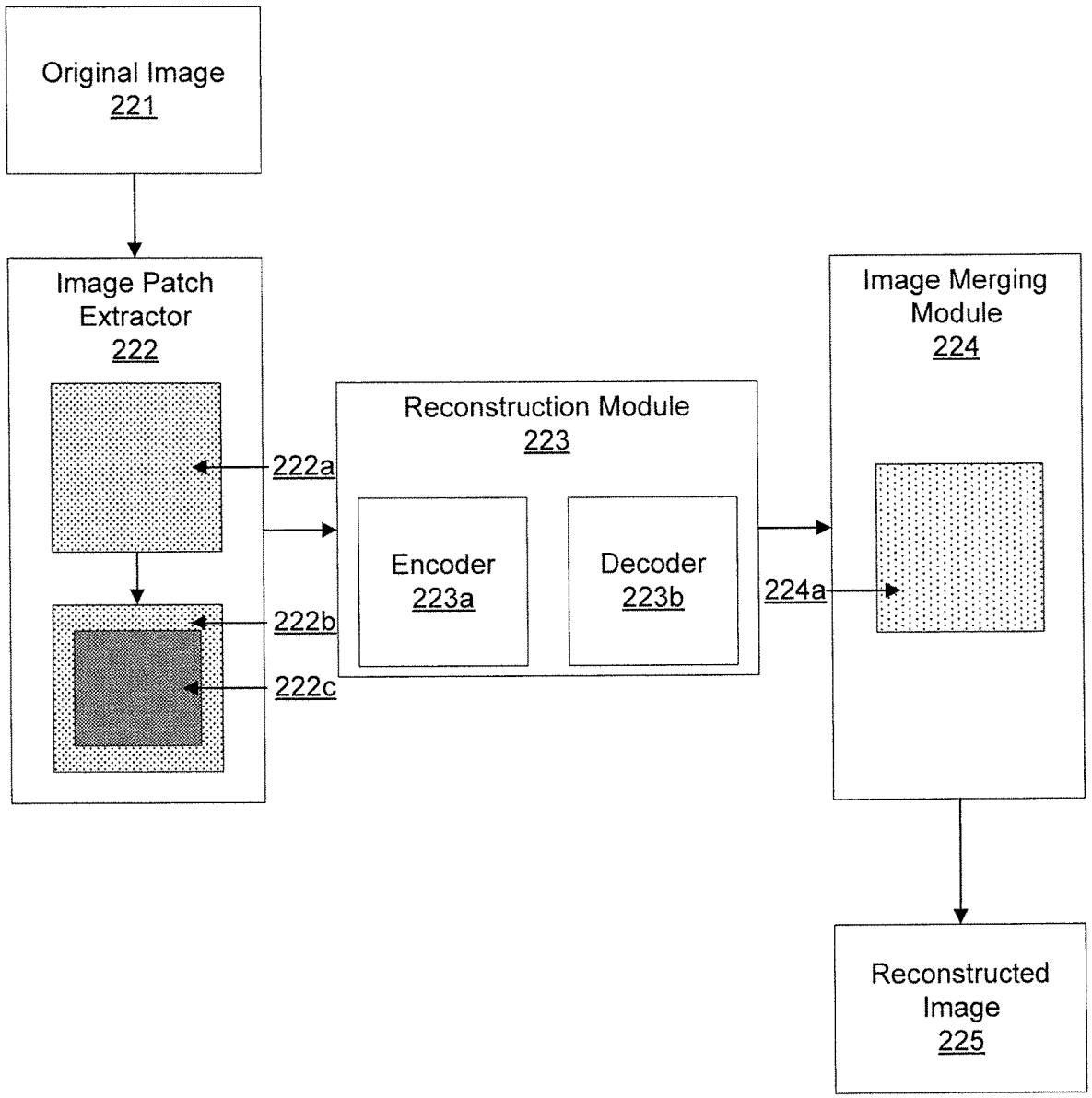
FIG. 4 is a block/flow diagram illustrating a system/method for reconstructing an image for detecting and correcting defects and anomalies, in accordance with the present principles.

Referring now to FIG. 4, a system/method for reconstructing an image for detecting and correcting defects and anomalies is illustratively depicted in accordance with the present principles.

The reconstructor 220 can reconstruct the original image 221 of the item to represent a defectless version of the item by extracting image patches (interchangeable referred to herein as "image patch portions" or "patch portions" in short) with an image patch extractor 222. The image patch extractor 222 can identify portions of the original image 221 to be reconstructed, such as, e.g., using a grid superimposed on the image. The image patch extractor 222 can then, using a processor, extract a series of image patches 222a from the original image 221, where each image patch 222a in the series is a different portion of the original image 221 according to the identified portions of the original image 221. To facilitate reconstruction of each image patch 222a, a region 222c in each image patch 222a is blacked-out or otherwise masked to generate a partially masked image patch 222b. In this way, data regarding features of the item in the original image 221 is removed from the image patches 222a so that reconstruction can be performed independent of any features present in corresponding portions of the original image 221.

For each image in the series, a reconstruction module 223 can reconstruct the masked region 222c of each partially masked image patch 222b. The reconstruction module 223 can, therefore, include, e.g., a processing device including a processor, and a storage device such as, e.g., a hard drive, solid state drive, a flash memory or a temporary memory, such as, e.g., a RAM, a buffer, or a cache. To reconstruct the masked region 222c, the reconstruction module 223 can utilize, e.g., an encoder-decoder arrangement stored in the storage device, or other suitable neural network for reconstructing images.

According to aspects of the present invention, the reconstruction module 223 is trained using defectless items of the type being analyzed. Thus, when the reconstruction module 223 reconstructs a masked region 222c for each partially masked image patch 222b of the original image 221, it does so based on defectless training by predicting the contents of the masked region 222c. As a result, the reconstructed portion will appear to be defectless in a reconstructed image patch. By training the reconstruction module 223 with defectless items, training images can be easily found. Thus, training of the reconstruction module 223 is quick and efficient, with a large training set facilitating improved accuracy. Moreover, by reconstructing images to be defectless, types of defects and anomalies do not need to be taken into account, thus reducing the complexity of the reconstruction, improving speed and efficiency of an anomaly detection and tagging system 200.

In embodiments of the present invention, the reconstruction module 223 employs an encoder-decoder arrangement including an encoder 223a and decoder 223b. Accordingly, the partially masked image patch 222b with a masked region 222c is provided to the encoder 223a, which transform the partially masked image patch 222b with a hidden layer to a latent representation in a feature space, such as, e.g., a multidimensional feature space vector. The hidden layer can include an activation function and a weight matrix. The encoder 223a can include one or more hidden layers to arrive at an encoded representation, such as, e.g., the multidimensional feature space vector. In addition to masking features of the image patches 222a, the encoder 423a can be configured to reduce the dimensionality of the representation to further obfuscate any features in unmasked regions of the image patches 223, and thus reduce the risk of anomalies being present in a reconstructed representation of the image patches 223.

The encoded representation can then be decoded by the decoder 223b to generate a predicted image patch 224a. Similar to the encoder 223a, the decoder 223b can use one or more hidden layers to transform the encoded representation to a representation corresponding to an output image by using an activation function and a weight matrix. The activation function and weight matrix of the decoder 223b can be the same or different from the activation function and weight matrix of the encoder 223a.

Because the partially masked image patch 222b includes a masked region 222c, the encoder 223a encodes the partially masked image patch 222b without any data related to any features of the item in the masked region 222c. Thus, the features of the corresponding portion of the item are not encoded in the multidimensional features space vector. As a result, the decoder 223b can then reconstruct the image patch 222a by predicting the masked region 222c without any influence from features of a corresponding portion of the original image 221. Thus, a defectless item can be predicted corresponding to the masked region 222c in an efficient manner.

Because the encoder 223a and decoder 223b have been trained with defectless items, the decoder 223b is trained to predict defectless features. Thus, the predicted image portion includes a reconstructed image patch 224a having no defects or anomalies, even if the corresponding image patch 222a of the original image 221 did have defects or anomalies.

The reconstructed image patch 224a can then be merged back into the original image 221 with the image merging module 224. The image merging module 224 can include, e.g., a processing device including a process, and a storage device such as, e.g., a hard drive, solid state drive, a flash memory or a temporary memory, such as, e.g., a RAM, a buffer, or a cache. The reconstructed image patch 224a will replace the corresponding portion of the original image 221 such that the original image 221 becomes a reconstructed image 225. Alternatively, the reconstructed image patch 224a can be stitched with other previously reconstructed image patches, independent of the original image. Each extracted image patch 222a will be reconstructed by the reconstruction module 223 and merged back into the image with the image merging module 224. Thus, the reconstructed image 225 will be produced with every identified portion replaced with a reconstructed version of that portion. As a result, the reconstructed image 225 will depict a defectless item. The reconstructed image 225 can then be stored, e.g., in a storage device such as, e.g., a hard drive, solid state drive, a flash memory or a temporary memory, such as, e.g., a RAM, a buffer, or a cache.

Figure 5:
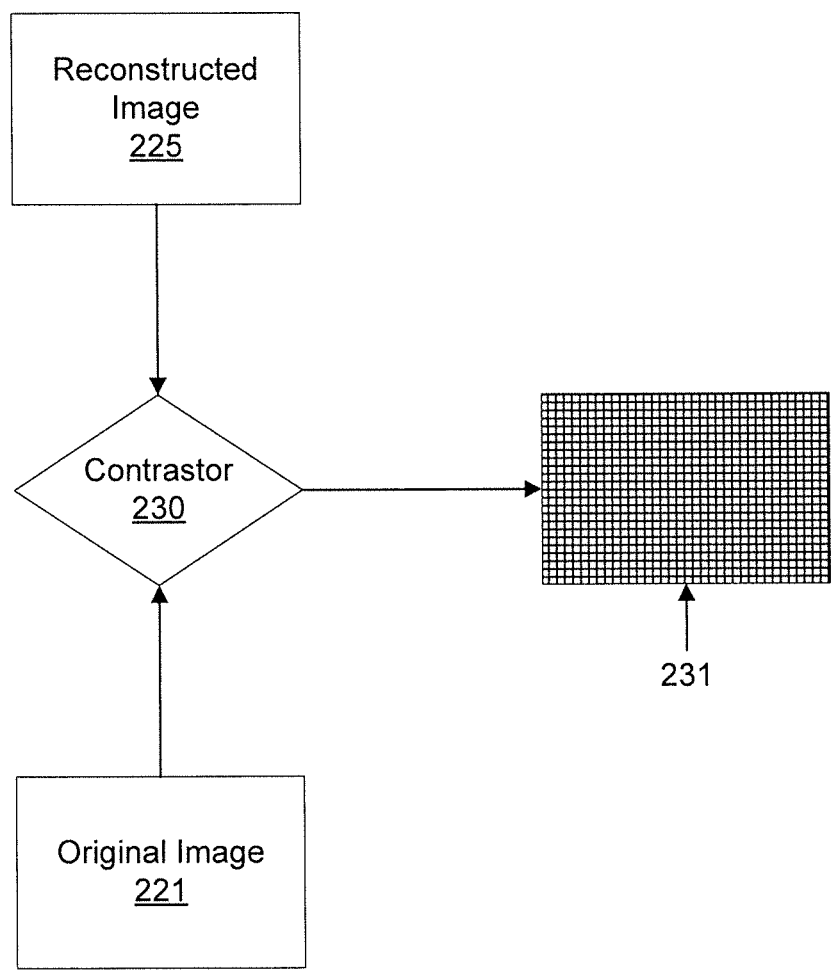
FIG. 5 is a block/flow diagram illustrating a system/method for contrasting a reconstructed image and original image for detecting and correcting defects and anomalies, in accordance with the present principles.

Referring now to FIG. 5, a system/method for contrasting a reconstructed image and original image for detecting and correcting defects and anomalies is illustratively depicted in accordance with the present principles.

A reconstructed image 225 can include an image having a number of portions of an original image 221 reconstructed by a reconstructor 220. Thus, as discussed above, the reconstructed image 225 will depict an item having any defects or anomalies removed by the reconstruction process. The reconstructed image 225 can be contrasted with the original image 221 by a contrastor 230 using, e.g., a processing device including a processor and a storage device, such as, e.g., a hard drive, a solid state drive, a flash memory, a RAM, a buffer or a cache. The contrastor 230 can, e.g., determine a pixel-by-pixel difference between the images to produce an anomaly map 231. Areas of high contrast between the two images will result in a larger difference of pixels at that location. That difference can be mapped to a new image depicting the pixel-by-pixel difference, thus highlighting the anomalies in an anomaly map 231.

Figure 6:
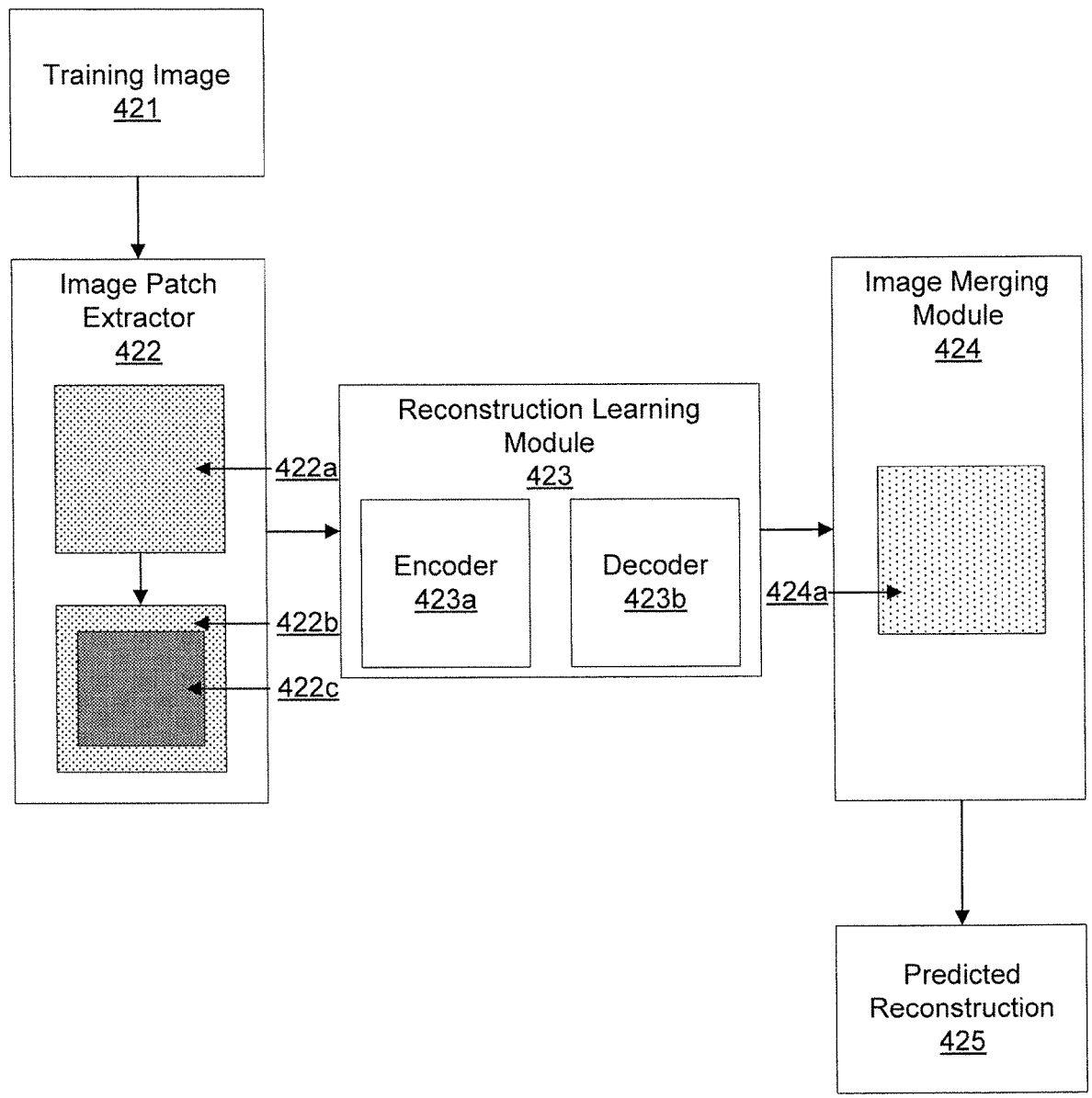
FIG. 6 is a block/flow diagram illustrating a system/method for training a reconstructor for detecting and correcting defects and anomalies, in accordance with the present principles.

Referring now to FIG. 6, a system/method for training a reconstructor for detecting and correcting defective items is illustratively depicted in accordance with the present principles.

A reconstructor can be trained to reconstruct images by training a reconstruction learning module 423 with training images 421. The training images 421 can each include an image of an item of a type to be analyzed by an anomaly detection and tagging system, such as the anomaly detection and tagging system 200 discussed above. Each training image 421 will be defectless, or in other words, "normal". Thus, the reconstruction learning module 423 is training to reconstruct defectless item images. By training the reconstruction training module 423 with defectless items, training images can be easily found. Thus, training of the reconstruction training module 423 is quick and efficient, with a large training set facilitating improved accuracy. Moreover, by reconstructing images to be defectless, types of defects and anomalies do not need to be taken into account, thus reducing the complexity of the reconstruction, improving speed and efficiency of an anomaly detection and tagging system 200.

To train the reconstruction learning module 423, an image patch extractor 422 will extract patches 422a of the training image 421. The image patch extractor 422, including a processing device having a processor, can identify portions of the training image 421 to be reconstructed, such as, e.g., using a grid superimposed on the image. The image patch extractor 422 can then extract a series of image patches 422a from the training image 421, where each image patch 422a in the series is a different portion of the training image 421 according to the identified portions of the training image 421 and temporarily or permanently store the image patches 422a in a cache or a buffer.

A portion of each image patch 422a can be blacked-out or otherwise masked to form a masked region 422c of the image patch 422a to generate a partially masked image patch 422b. This masked region 422c contains no data regarding any features of a corresponding portion of the training image 421. Thus, reconstruction of each partially masked image patch 422b can be performed independent of any features of the training image 421.

For each image in the series, a reconstruction learning module 423 can reconstruct the masked region 422c of each partially masked image patch 422b. The reconstruction learning module 423 can, therefore, include, e.g., a processing device including a processor, and a storage device such as, e.g., a hard drive, solid state drive, a flash memory or a temporary memory, such as, e.g., a RAM, a buffer, or a cache. To reconstruct the masked region 422c, the reconstruction learning module 423 can utilize, e.g., an encoder-decoder arrangement stored in the storage device, or other suitable neural network for reconstructing images.

Accordingly, the partially masked image patch 422b is provided to the encoder 423a, which transforms the masked region 422c with a hidden layer to a latent representation in a feature space, such as, e.g., a multidimensional feature space vector. The hidden layer can include an activation function and a weight matrix. The encoder 423a can include one or more hidden layers to arrive at an encoded representation, such as, e.g., the multidimensional feature space vector. Because the reconstruction learning module 423 is trained with partially masked images 422b, it is unnecessary to reduce the dimensionality of the multidimensional features space vector to below that of an identity function. However, reducing the encoder 423a can be configured to reduce the dimensionality of the representation to further obfuscate any features in unmasked regions of the image patches 423, and thus reduce the risk of anomalies being present in a reconstructed representation of the image patches 223.

The encoded representation can then be decoded by the decoder 423b to generate a predicted image patch 424a. Similar to the encoder 423a, the decoder 423b can use one or more hidden layers to transform the encoded representation to a representation corresponding to an output image by using an activation function and a weight matrix. The activation function and weight matrix of the decoder 423b can be the same or different from the activation function and weight matrix of the encoder 423a.

Because the reconstruction learning module 423 is trained with partially masked images 423, the reconstruction learning module 423 learns reconstruction for image patches by predicting data independent from any preexisting data in the masked portion 422c. Complexity is, therefore, reduced for encoding and decoding, improving the speed and efficiency of the image reconstruction.

The predicted image can then be compared with the input image. An error can be determined according to difference between the input image and predicted image using a loss function. The error can be backpropagate to each hidden layer of the encoder 423a and decoder 423b to update the weight matrices at each layer using a suitable backpropagation process, such as, e.g., a gradient descent method, or a conjugate gradient method, among other backpropagation methods. This process is repeated with multiple training images. The training images will correspond to portions of images of defectless items of the type to be reconstructed. For example, the reconstruction learning module 423 can be trained with manufactured products to reconstruct images of manufactured products. Thus, the encoder-decoder arrangement of the reconstruction learning module 423 will be trained to reconstruct images of defectless items.

While, the training can be performed as an independent process to train the reconstruction learning module 423 prior to implementing the reconstruction learning module 423 as a reconstructing module, such as the reconstruction module 223 discussed above, the reconstruction module can be trained concurrently as a reconstruction learning module 423 with implementing the reconstruction module to reconstruct product images.

Therefore, while reconstructing image portions of a product, a reconstruction module, such as the reconstruction learning module 423 can reconstruct the image patches 422a. The reconstructed image patches 424a can then be merged back into the training image 421 with the image merging module 424. The reconstructed image patch 424a will replace the corresponding image patch 424a of the training image 421 such that the training image 421 becomes a predicted reconstruction 425. Each extracted image patch 422a will be reconstructed by the reconstruction learning module 423 and merged back into the image with the image merging module 424. Thus, the predicted reconstruction 425 can be produced with every identified portion replaced with a reconstructed version of that portion.

The reconstruction version can be contrasted with the original image using a process and system, such as the contrastor 230 and anomaly tagging module 240 described above. If the original image is found to be defect-free, the reconstructed portions can be used to determine an error with, e.g., a loss function, and backpropagate that error to the hidden layers of the reconstruction learning module 423, as discussed above. Thus, the reconstruction learning module 423 can continuously be trained with defect-free product images while concurrently determining if a product has defects.

Figure 7:
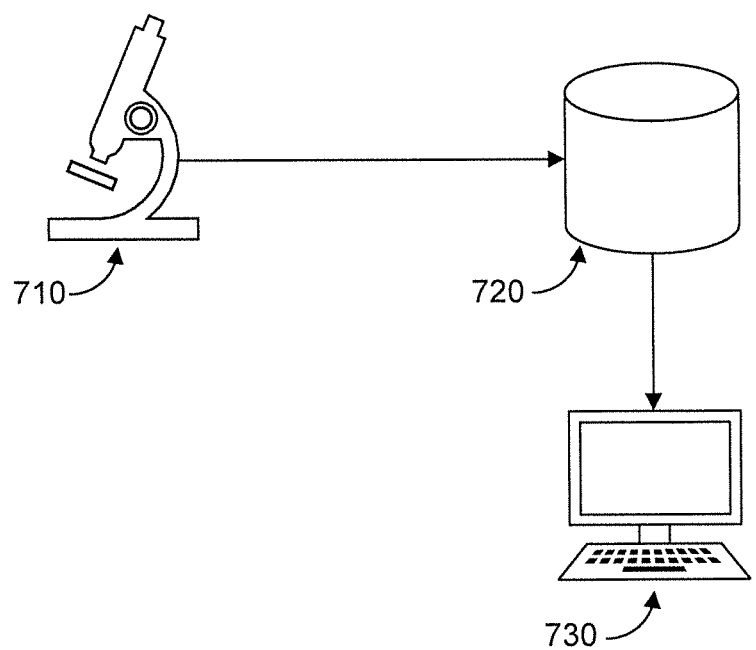
FIG. 7 is a block/flow diagram illustrating a high-level system/method for diagnosing medical anomalies, in accordance with the present principles.

Referring now to FIG. 7, a high-level system/method for diagnosing medical anomalies, in accordance with the present principles is illustratively depicted in accordance with the present principles.

In one embodiment, a medical scanning device 710 generates scans of a person's anatomy, such as, e.g., an X-ray sensor, a magnetic resonance imaging (MRI) device, a computed tomography (CT) scan, a positron emission tomography (PET) scan, optical image, or other scanning device suitable for medical diagnosis. The medical scanning device 710 can, therefore, generate an image of anatomy or physiology. A person's anatomy or physiology can sometimes contain an anomaly that may indicate a disease or condition needing treatment. Thus, the image can be provided to a medical anomaly detection system 720.

The medical anomaly detection system 720 will inspect the anatomy scans to determine if there are any anomalies. Such anomalies can include, e.g., physical signs and symptoms in anatomy and physiology that indicate a medical abnormality including, e.g., a tumor, a blood clot, a broken bone, a dislocation, a fracture, among others. The medical anomaly detection system 720 can determine that an abnormality exists by comparing the scans to a scan that of normal anatomy and physiology. For example, e.g., the medical anomaly detection system 720 can include a machine learning system that is trained with images of medically normal patient anatomy and physiology. By training the system with normal patient scans, the medical anomaly detection system 720 can generate a reconstruction of the anatomy scans that does not contain any abnormalities, and compare the reconstructed version with the original scans to identify differences. The locations of the differences will indicate an anomaly in anatomy or physiology. These differences can, therefore, be identified with the medical anomaly detection system 720.

The identified abnormalities can be communicated to a diagnosis system 730, such as, e.g., a display, computer, or other notification device. Thus, the diagnosis system 730 can notify a doctor of the abnormalities. Therefore, the doctor can easily and quickly find anomalies in a patient's anatomy that may have otherwise gone unnoticed or undetected. Alternatively, the diagnosis system 730 can include a device for automatically administering a medication. For example, where the medical scanning device 710 is an X-ray device, an anomaly may correspond to a broken bone. Thus, the diagnosis system 730 can, e.g., automatically administer a pain killer in response to tagging a bone related anomaly.

Figure 8:
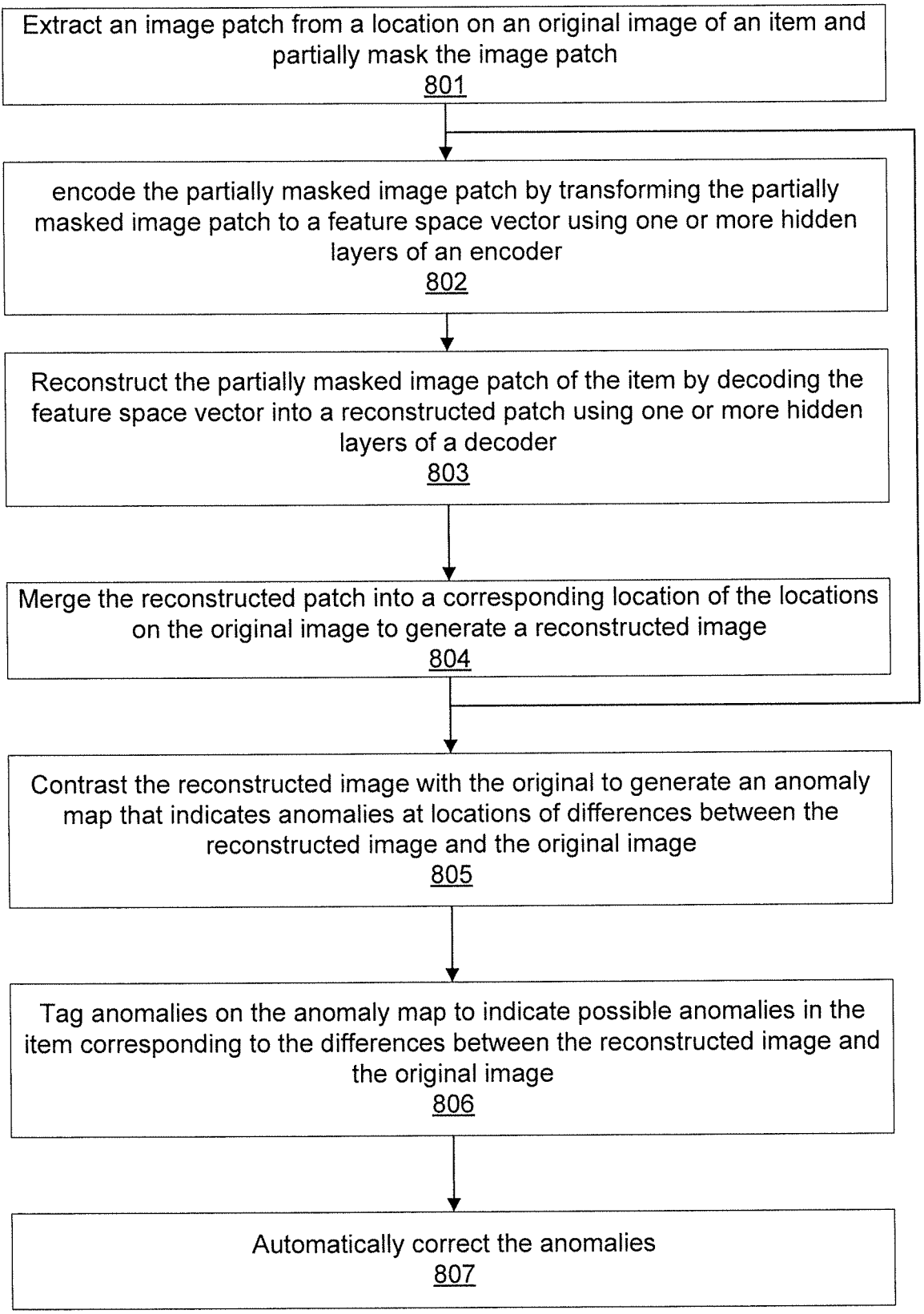
FIG. 8 is a flow diagram illustrating a system/method for detecting defects and anomalies with a reconstructor and contrastor, in accordance with the present principles.

Referring now to FIG. 8, a system/method for detecting defects and anomalies with a reconstructor and contrastor is illustratively depicted in accordance with the present principles.

At block 801, extract an image patch from a location on an original image of an item and partially mask the image patch.

The original image can be captured with an imaging device, such as, e.g., a camera, CCD, infrared sensor, LIDAR sensor, or other device for capturing images. The original image will be an image of the item, such as, e.g., a manufactured product, or a part of anatomy, among other items. Occasionally, the item will include defects and anomalies that undesired, such as, e.g., cracks, burrs, protrusions, dents, etc. The image device will capture these anomalies and defects.

Portions of the original image can then be identified to be reconstructed, such as, e.g., using a grid superimposed on the image. The portions are then extracted as a series of image patches from the original image, where each image patch in the series is a different portion of the original image according to the identified portions of the original image. To hide an area of the portions so that the area can be reconstructed, the area can be masked by, e.g., blacking-out, hiding, or otherwise removing the area from subsequent processing.

At block 802, encode the partially masked image patch by transforming the partially masked image patch to a feature space vector using one or more hidden layers of an encoder.

In embodiments of the present invention, the image patch is provided to an encoder, which transform the image patch with a hidden layer to a feature space vector. The hidden layer can include an activation function and a weight matrix. The encoder can include one or more hidden layers to arrive at the feature space vector.

At block 803, reconstruct the partially masked image patch of the item by decoding the feature space vector into a reconstructed patch using one or more hidden layers of a decoder.

The encoded representation can then be decoded by a decoder to generate a predicted image patch that returns the encoded representation back to a representation having the original number of dimensions of the input image patch. Similar to the encoder, the decoder can use one or more hidden layers to transform the encoded representation to a representation corresponding to an output image patch by using an activation function and a weight matrix. The activation function and weight matrix of the decoder can be the same or different from the activation function and weight matrix of the encoder.

Because the encoder encodes a partially masked image portion, the decoder predicts a masked region of the partially masked image portion. Thus, contents, including, e.g., physical or visible features of image patch used as the input image patch, are predicted during decoding by the decoder without influence from any features of the original image of the item. As a result, the output representation including the predicted image patch reconstructs the image patch according to the weight matrix and activation function.

At block 804, merge the reconstructed patch into the location on the original image to generate a reconstructed image.

The reconstructed image patch can then be merged back into the original image. The reconstructed image patch will replace the corresponding portion of the original image such that the original image becomes a reconstructed image. Alternatively, the reconstructed image patch can be stitched with other previously reconstructed image patches, independent of the original image.

Each extracted image portion will be reconstructed and merged back into the image. Thus, the reconstructed image will be produced with every extracted patch replaced with a corresponding reconstructed patch. As a result, the reconstructed image will depict a defectless item. The reconstructed image can then be stored, e.g., in a storage device such as, e.g., a hard drive, solid state drive, a flash memory or a temporary memory, such as, e.g., a RAM, a buffer, or a cache.

At block 805, contrast the reconstructed image with the original to generate an anomaly map that indicates anomalies at locations of differences between the reconstructed image and the original image.

To determine anomalies and defects in the item, the reconstructed image can then be compared to the original image with a contrastor. The contrastor can compare the reconstructed image with the original image by, e.g., performing a pixel-by-pixel difference between the images. However, other contrasting methods are contemplated. Because of the contrasting, the differences between the reconstructed image and original image can be mapped in an anomaly map that represents a degree of difference between the reconstructed image and the original image at each location. The anomaly map can take the form of, e.g., a visual representation, such as an image, or a matrix representation, or by any other suitable representation. As a result, the anomaly map can take the form of separate representation of the item, or it can be overlaid onto the original image to provide both a representation of the actual item, as well as a representation of the anomalies.

At block 806, tag anomalies on the anomaly map to indicate possible anomalies in the item corresponding to the differences between the reconstructed image and the original image.

The anomaly map can then be used to identify anomalies by tagging areas of greatest difference between the reconstructed image and the original image corresponding to the results in the anomaly map. Tagged areas can be determined according to, e.g., an anomaly threshold value that represents degree of difference between the reconstructed image and the original image. If an area has a difference as represented in the anomaly of greater than the anomaly threshold, then that area can be tagged as containing an anomaly on a corresponding location of the item. Thus, item defects and anomalies can be identified. The anomaly tags can be applied to, e.g., the anomaly map, the original image, or both, or as a separate representation, such as, e.g., a list with coordinates.

At block 807, automatically correct the anomalies.

In response to the anomaly map and the anomaly tags, corrective action can be taken. For example, a product having anomalies indicating defects can be automatically removed from a production line, or the entire production line can be automatically stopped. As another possible corrective action, a notification can be provided to an operator via a notification system, such as, e.g., a display or audible alert, such that the operator can take an appropriate action.

A description will now be given regarding embodiments of the present invention directed to anomaly detection with predictive normalization.

In the field of anomaly detection on images, there is always a scarcity of positive (anomalous) examples. However, negative (normal) examples are generally widely available. This invention makes use of the large amount of negative examples to train a model to enhance defects with respect to its surroundings so that a subsequent traditional supervised model can be trained with higher accuracy. Assuming that the rough size of the defects are known, we train a contextual auto-encoder (CAE) model with the context size being larger than the prediction size which corresponds to the approximate size of a defect. The CAE is trained with negative examples only and then used to normalize images that are used for training the supervised classifier. This normalization step is key to increase accuracy of the model and we observe an increase of 15 percentage points on the area under Precision-Recall curve (AUPRC).

Figure 9:
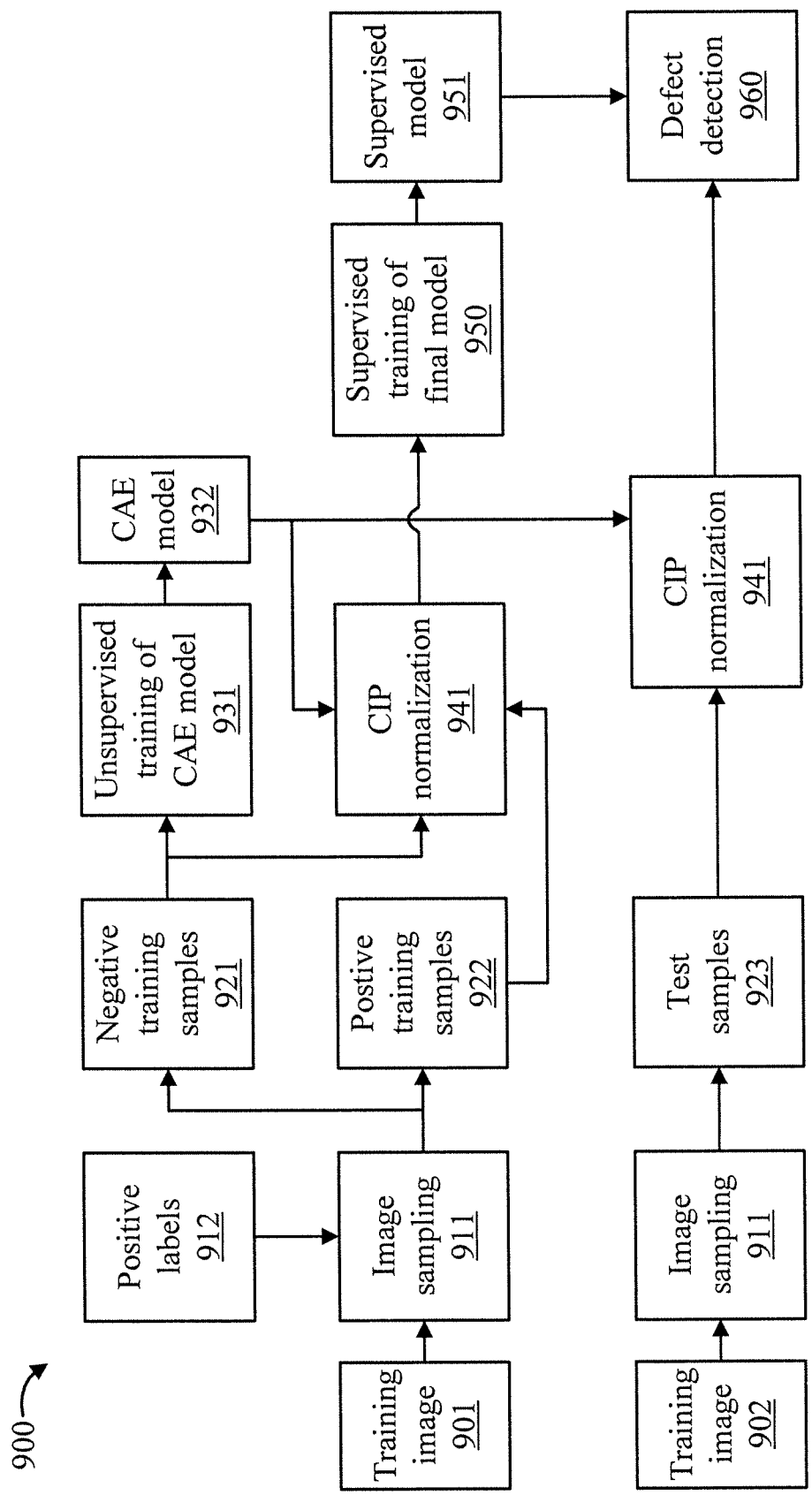
FIG. 9 is a block/flow diagram illustrating a high-level system/method for anomaly detection with predictive normalization, in accordance with an embodiment of the present invention.

FIG. 9 is a block/flow diagram illustrating a high-level system/method for anomaly detection with predictive normalization, in accordance with an embodiment of the present invention. During an offline phase, training image(s) are first sampled by cutting out image samples of the size defined by the CAE model. Positive labels 912 indicate the position and shape of ground-truth defects on the image. Negative samples 921 are extracted at valid positions on the image, avoiding areas of positive samples. The CAE model 932 is then trained using the negative samples. For the supervised training phase, both negative and positive samples are extracted from the training image(s) and CIP normalization is applied 941. The normalized samples are then used to train the supervised model 951.

For the online phase, samples are extracted from test image(s) 902 and CIP normalization is applied. The normalized samples are then sent to the defect detection module 960, where the supervised model 951 is applied to classify samples as normal or defect and where corrective action may be taken.

The image sampling module 911 extracts image samples of a certain size from the image. The size of the image samples is dictated by the size of the input of the model. The location of the samples is decided by a sampling strategy. One simple strategy, for example is pure random. Other strategies may involve preferring samples that exhibit large variance in luminance (the goal being to avoid flat featureless areas). Invalid parts of the image may also be ignored by the sampling process. Such parts may lie outside the marking of the contour of an object, for example. For the CAE training phase, areas of labeled defects should also be avoided. For the supervised training phase, the sampling module 911 extracts positive and negative samples from defect areas and normal areas respectively. Given that the number of positive labels is usually small, it is often desirable to generate as many positive examples as possible from a given label. A strategy is to sample in a grid fashion around the label such that the labeled defect is contained fully or partially within the image sample. Further augmentations may be applied, such as horizontal or vertical axis flips, 90-degree rotations and combinations of both. Such operations preserve the pixel intensities within the image sample. Non-preserving operations may also be applied such as free rotations or warping.

The unsupervised training module 931 which produces the CAE classifier model 932 is a contextual auto-encoder module. It includes two parts. First an encoder takes as input an image sample and compresses it via a convolutional neural network into a lower-dimensional vector of number (a code). Second, a decoder takes as input the code vector produced by the encoder and expands it via a convolutional neural network into an image. The parameters of the network (a.k.a. weights) are then gradually adjusted using the backpropagation procedure so as to minimize a loss function. The loss function can be, for example, the mean of squared differences between the output of the decoder and the center patch of the input image.

Figure 10:
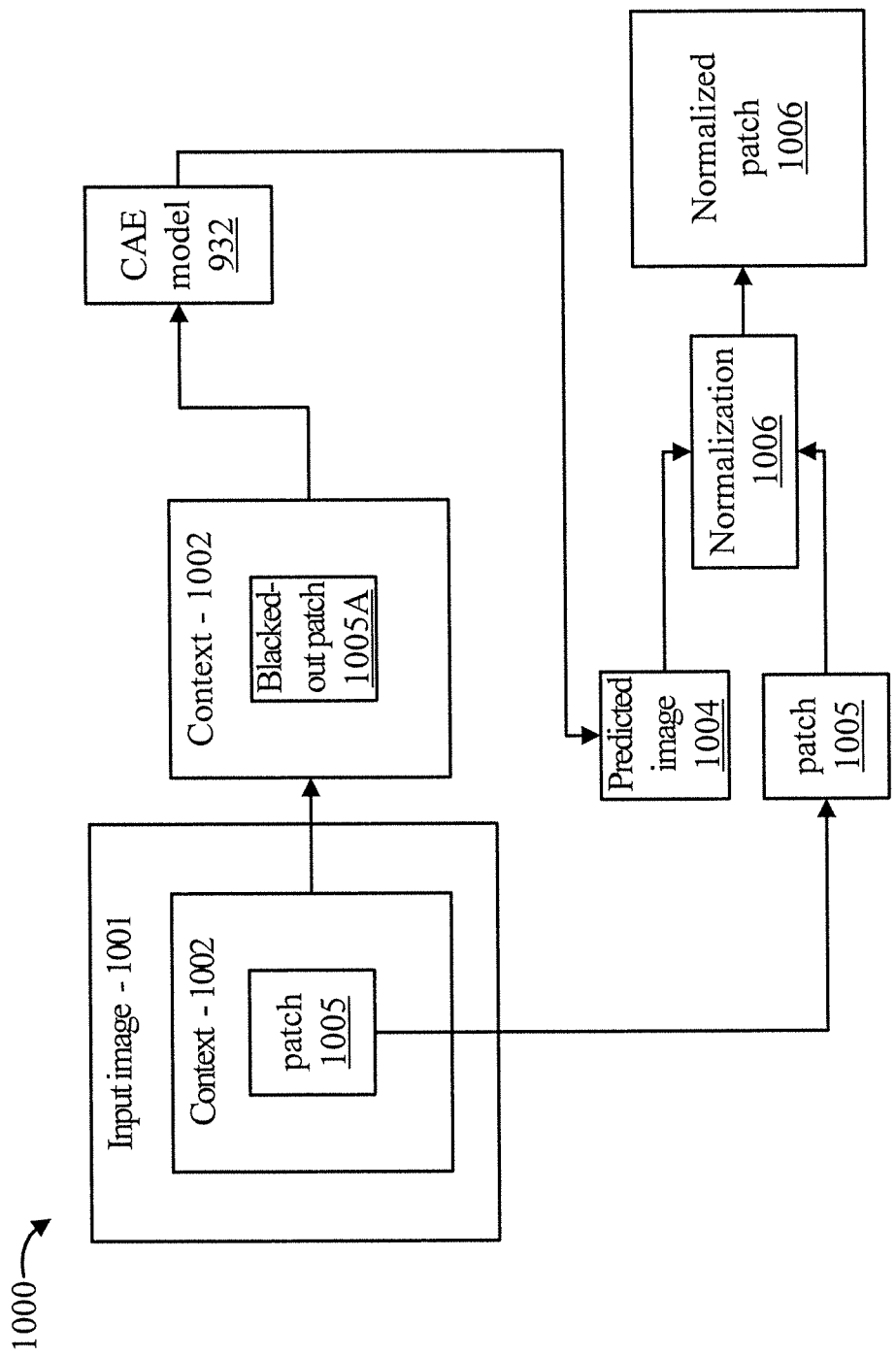
FIG. 10 is a diagram further illustrating the CIP normalization module of FIG. 9, in accordance with an embodiment of the present invention.

FIG. 10 is a diagram further showing the CIP normalization module 941 of FIG. 9, in accordance with an embodiment of the present invention.

An input image sample 1001 includes a center patch 1005 and its surrounding context 1002. The size of the patch is decided based on the knowledge of the rough size of defects. For example, a size of 32×32 pixels may be used for the center patch and a size of 64×64 pixels may be used for the context. The center patch is blacked-out 1005A (its values set to 0) and the image sample is presented to the CAE model 932 for inference, which produces the center patch 1004. The predicted center patch 1004 is then sent together with the center patch 1005 to the normalization module 1006, which produces a normalized center patch 1007. The normalization module 1006 can include any operation combining both input images into a normalized output. For example, the predicted center patch 1004 may be subtracted, component-wise, from the input center patch 1005. Further operations may be applied by normalization module 1006, such as remapping the pixel intensities so that their new range makes the subsequent supervised learning procedure more efficient. A pixel intensity range of [−1;+1] is usually optimal. The mapping parameters may be obtained from the center patch itself or from the entire training set of center patches.

Referring back to FIG. 9, the supervised training of final model module 950 performs the supervised training of the final classifier model 951. For this model a standard deep convolutional network (CNN), or any other appropriate classifier such as a support vector machine (SVM) can be utilized. The model is trained with positive and negative examples that were both normalized by the CIP normalization module 941 described above. Once trained, the model is used by the defect detection module 960 to predict whether a given normalized example is normal or not. Further actions may be taken by the defect detection module 960 if necessary. For example, if the number of defective examples in an image is above a certain threshold, the image maybe flagged for review, a corresponding product may be discarded or repaired, and so forth.

Figure 11:
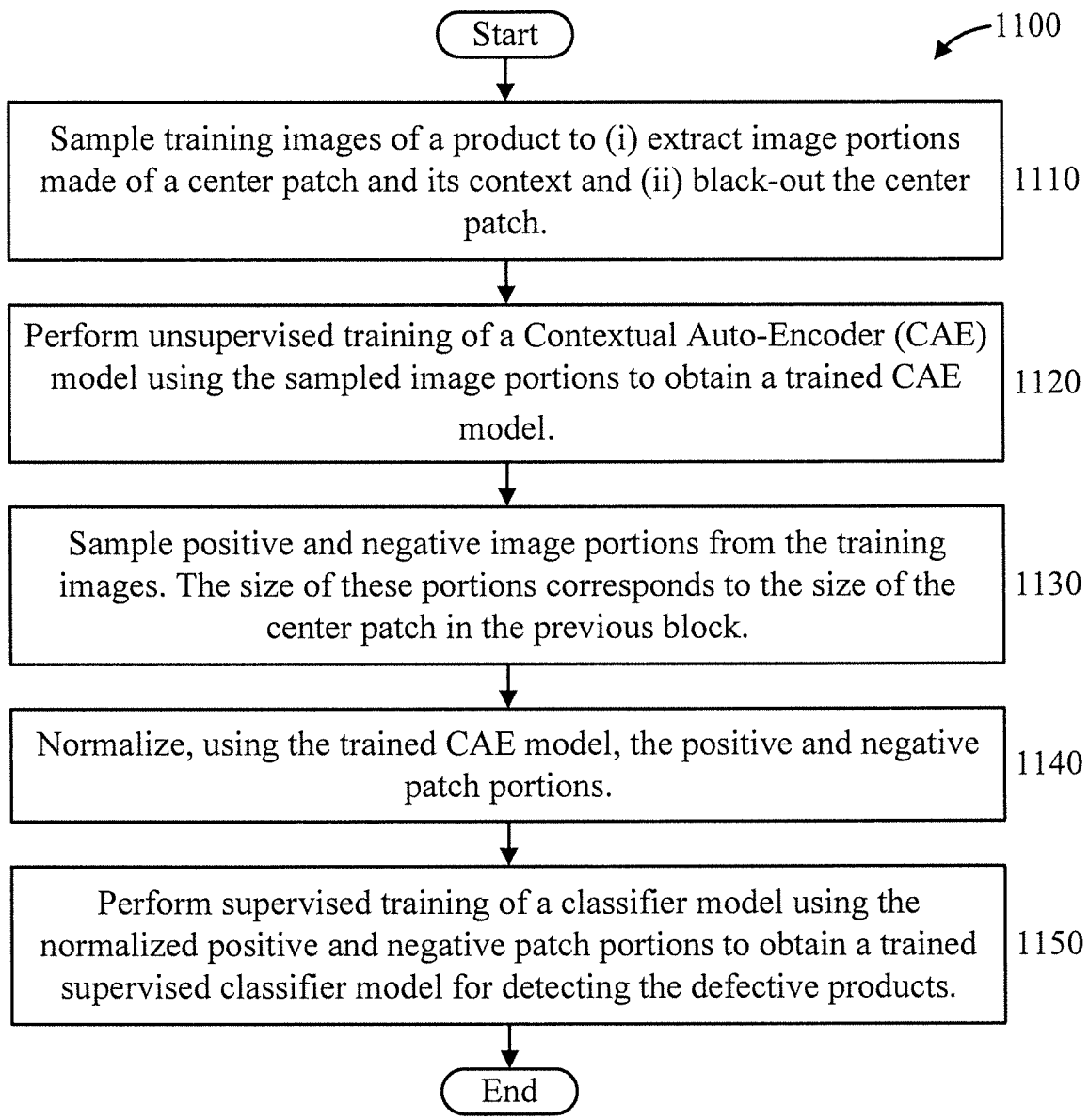
FIG. 11 is a flow diagram illustrating a method for training an anomaly detector with predictive normalization, in accordance with an embodiment of the present invention.

FIG. 11 is a flow diagram illustrating a method 1100 for training an anomaly detector with predictive normalization, in accordance with an embodiment of the present invention.

At block 1110, sample training images of a product to (i) extract image portions made of a center patch and its context and (ii) black-out the center patch. In an embodiment, the training images are sampled at random positions. However, other sampling approaches can be used, while maintaining the spirit of the present invention.

In an embodiment, block 1110 can involve (i) avoiding invalid areas, (ii) avoiding areas that include positive labels indicative of an anomaly, and (iii) favoring the portions for extraction that exhibit a pixel intensity variance higher than other portions while maintaining a threshold amount of randomness.

At block 1120, perform unsupervised training of a Contextual Auto-Encoder (CAE) model using the sampled image portions to obtain a trained CAE model. In an embodiment, the unsupervised training can be performed using a mean of squared pixel intensity differences as a loss function.

At block 1130, sample positive and negative image portions from the training images. The size of these portions corresponds to the size of the center patch in the previous block.

In an embodiment, block 1130 can involve (i) avoiding invalid areas, (ii) augmenting the positive and negative patch portions by combinations of a horizontal axis flip, a vertical axis flip, and 90 degree rotations, and (iii) augmenting the positive and negative samples by combinations of free rotations and warping.

At block 1140, normalize, using the trained CAE model, the positive and negative patch portions.

In an embodiment, the normalization step in block 1140 can involve subtracting a patch predicted by the CAE model from the corresponding input patch, and further involve applying pixel intensity remapping. In an embodiment, the pixel intensity remapping can be determined based on intensity statistics of the patch itself and/or based on intensity statistics of several patches from the training set. The statistics can include, but are not limited to, for example, mean, standard deviation, minimum, maximum, percentiles, and so forth.

At block 1150, perform supervised training of a classifier model using the normalized positive and negative patch portions to obtain a trained supervised classifier model for detecting the defective products.

Figure 12:
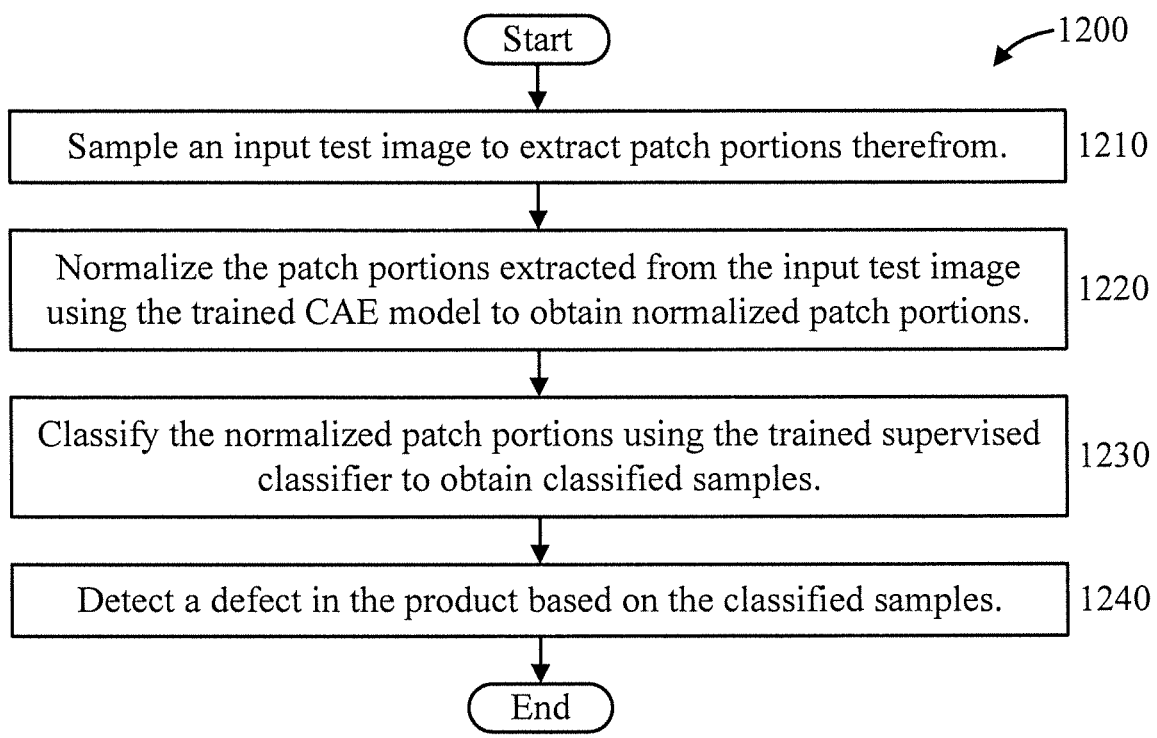
FIG. 12 is a flow diagram illustrating a method for using a trained anomaly detector with predictive normalization, in accordance with an embodiment of the present invention.

FIG. 12 is a flow diagram illustrating a method 1200 for using a trained anomaly detector with predictive normalization, in accordance with an embodiment of the present invention.

At block 1210, sample an input test image to extract patch portions therefrom.

At block 1220, normalize the patch portions extracted from the input test image using the trained CAE model to obtain normalized patch portions.

At block 1230, classify the normalized patch portions using the trained supervised classifier to obtain classified samples.

In an embodiment, the classifying block (1230) is performed using a Deep Convolutional Neural Network (DCNN) to output a classification score, and wherein a particular one of the patch portions is deemed defective responsive to the particular one of the patch portions having the classification score below a threshold.

In an embodiment, the classifying block (1230) aggregates classifications of all of the patch portions sampled from the input test image, classifies the input test image as including a defect responsive to a number of defective ones of the patch portions sampled from the input test image exceeding a threshold, and displays locations of the patch portions including the detect by overlaying identifying information on the input test image.

At block 1240, detect a defect in the product based on the classified samples.

At block 1250, perform an action responsive to a detection of a defect. For example, the product may be discarded, a corrective action performed (e.g., replace the defective portion), a location of a defect(s) indicated on an overlay image over an image of a defective product, and so forth.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for model training to detect defective products, the method comprising:

sampling, by a hardware processor, training images of a product to (i) extract image portions therefrom made of a center patch and its context and (ii) black-out the center patch;

performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;

sampling, by the hardware processor, positive and negative center-patch-sized portions from the training images;

normalizing, by the hardware processor using the trained CAE model, the positive and negative center-patch-sized portions;

performing, by the hardware processor, supervised training of a classifier model using the normalized positive and negative center-patch-sized portions to obtain a trained supervised classifier model for detecting the defective products;

sampling an input test image to extract patch portions therefrom;

normalizing the patch portions extracted from the input test image using the trained CAE model to obtain normalized patch portions;

classifying the normalized patch portions using the trained supervised classifier to obtain classified samples; and detecting a defect in the product based on the classified samples;

wherein said classifying step is performed using a Deep Convolutional Neural Network (DCNN) to output a classification score, and wherein a particular one of the patch portions is deemed defective responsive to the particular one of the patch portions having the classification score below a threshold.

2. A computer-implemented method for model training to detect defective products, the method comprising:

sampling, by a hardware processor, training images of a product to (i) extract image portions therefrom made of a center patch and its context and (ii) black-out the center patch;

performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;

sampling, by the hardware processor, positive and negative center-patch-sized portions from the training images;

normalizing, by the hardware processor using the trained CAE model, the positive and negative center-patch-sized portions;

performing, by the hardware processor, supervised training of a classifier model using the normalized positive and negative center-patch-sized portions to obtain a trained supervised classifier model for detecting the defective products;

sampling an input test image to extract patch portions therefrom;

normalizing the patch portions extracted from the input test image using the trained CAE model to obtain normalized patch portions;

classifying the normalized patch portions using the trained supervised classifier to obtain classified samples; and detecting a defect in the product based on the classified samples;

wherein said classifying step is performed by:

aggregating classifications of all patches sampled from the input test image and labeling the input test image as defective responsive to a number of patches classified as defective being above a certain threshold; and displaying locations and information of defective patches by overlaying the information over the input test image.

3. A computer-implemented method for model training to detect defective products, the method comprising:

sampling, by a hardware processor, training images of a product to (i) extract image portions therefrom made of a center patch and its context and (ii) black-out the center patch;

performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;

sampling, by the hardware processor, positive and negative center-patch-sized portions from the training images;

normalizing, by the hardware processor using the trained CAE model, the positive and negative center-patch-sized portions; and performing, by the hardware processor, supervised training of a classifier model using the normalized positive and negative center-patch-sized portions to obtain a trained supervised classifier model for detecting the defective products;

wherein said step of sampling the training images comprises (i) avoiding invalid areas, (ii) avoiding areas that include positive labels indicative of an anomaly, and (iii) favoring the portions for extraction that exhibit a pixel intensity variance higher than other portions while maintaining a threshold amount of randomness.

4. A computer-implemented method for model training to detect defective products, the method comprising:

sampling, by a hardware processor, training images of a product to (i) extract image portions therefrom made of a center patch and its context and (ii) black-out the center patch;

performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;

sampling, by the hardware processor, positive and negative center-patch-sized portions from the training images;

normalizing, by the hardware processor using the trained CAE model, the positive and negative center-patch-sized portions; and performing, by the hardware processor, supervised training of a classifier model using the normalized positive and negative center-patch-sized portions to obtain a trained supervised classifier model for detecting the defective products;

wherein said step of sampling the positive and negative center-patch-sized portions comprises (i) avoiding invalid areas, (ii) augmenting the positive and negative patch portions by combinations of a horizontal axis flip, a vertical axis flip, and 90 degree rotations, and (iii) augmenting the positive and negative samples by combinations of free rotations and warping.

5. A computer-implemented method for model training to detect defective products, the method comprising:
sampling, by a hardware processor, training images of a product to (i) extract image portions therefrom made of a center patch and its context and (ii) black-out the center patch;
performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;
sampling, by the hardware processor, positive and negative center-patch-sized portions from the training images;
normalizing, by the hardware processor using the trained CAE model, the positive and negative center-patch-sized portions; and
performing, by the hardware processor, supervised training of a classifier model using the normalized positive and negative center-patch-sized portions to obtain a trained supervised classifier model for detecting the defective products;
wherein said normalizing step comprises:
subtracting a patch predicted by the CAE model from the corresponding input patch, and applying pixel intensity remapping.

6. The computer-implemented method of claim 5, wherein said applying step comprises determining a pixel intensity remapping based on intensity statistics of the patch itself.

7. The computer-implemented method of claim 5, wherein said applying step comprises determining a pixel intensity remapping based on intensity statistics of several of the center patches extracted from the training images.

8. A computer program product for model training to detect defective products, the computer program product comprising a non-transitory computer readable storage medium having program instructions embodied therewith, the program instructions executable by a computer to cause the computer to perform a method comprising:
sampling, by a hardware processor of the computer, training images of a product to (i) extract image portions therefrom made of a center patch and its context and (ii) black-out the center patch;
performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;
sampling, by the hardware processor, positive and negative center-patch-sized portions from the training images;
normalizing, by the hardware processor using the trained CAE model, the positive and negative center-patch-sized portions; and
performing, by the hardware processor, supervised training of a classifier model using the normalized positive and negative center-patch-sized portions to obtain a trained supervised classifier model for detecting the defective products;
wherein the method further comprises:
sampling an input test image to extract patch portions therefrom;
normalizing the patch portions extracted from the input test image using the trained CAE model to obtain normalized patch portions;
classifying the normalized patch portions using the trained supervised classifier to obtain classified samples; and
detecting a defect in the product based on the classified samples;
wherein said classifying step is performed using a Deep Convolutional Neural Network (DCNN) to output a classification score, and wherein a particular one of the patch portions is deemed defective responsive to the particular one of the patch portions having the classification score below a threshold.

9. A computer program product for model training to detect defective products, the computer program product comprising a non-transitory computer readable storage medium having program instructions embodied therewith, the program instructions executable by a computer to cause the computer to perform a method comprising:
sampling, by a hardware processor of the computer, training images of a product to (i) extract image portions therefrom made of a center patch and its context and (ii) black-out the center patch;
performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;
sampling, by the hardware processor, positive and negative center-patch-sized portions from the training images;
normalizing, by the hardware processor using the trained CAE model, the positive and negative center-patch-sized portions; and
performing, by the hardware processor, supervised training of a classifier model using the normalized positive and negative center-patch-sized portions to obtain a trained supervised classifier model for detecting the defective products;
wherein the method further comprises:
sampling an input test image to extract patch portions therefrom;
normalizing the patch portions extracted from the input test image using the trained CAE model to obtain normalized patch portions;
classifying the normalized patch portions using the trained supervised classifier to obtain classified samples; and
detecting a defect in the product based on the classified samples;
wherein said classifying step is performed by:
aggregating classifications of all patches sampled from the input test image and labeling the input test image as defective responsive to a number of patches classified as defective being above a certain threshold; and
displaying locations and information of defective patches by overlaying the information over the input test image.

10. A computer program product for model training to detect defective products, the computer program product comprising a non-transitory computer readable storage medium having program instructions embodied therewith, the program instructions executable by a computer to cause the computer to perform a method comprising:

sampling, by a hardware processor of the computer, training images of a product to (i) extract image portions therefrom made of a center patch and its context and (ii) black-out the center patch;
performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;
sampling, by the hardware processor, positive and negative center-patch-sized portions from the training images;
normalizing, by the hardware processor using the trained CAE model, the positive and negative center-patch-sized portions; and
performing, by the hardware processor, supervised training of a classifier model using the normalized positive and negative center-patch-sized portions to obtain a trained supervised classifier model for detecting the defective products;
wherein said step of sampling the training images comprises (i) avoiding invalid areas, (ii) avoiding areas that include positive labels indicative of an anomaly, and (iii) favoring the portions for extraction that exhibit a pixel intensity variance higher than other portions while maintaining a threshold amount of randomness.

11. A computer program product for model training to detect defective products, the computer program product comprising a non-transitory computer readable storage medium having program instructions embodied therewith, the program instructions executable by a computer to cause the computer to perform a method comprising:
sampling, by a hardware processor of the computer, training images of a product to (i) extract image portions therefrom made of a center patch and its context and (ii) black-out the center patch;
performing, by the hardware processor, unsupervised back-propagation training of a Contextual Auto-Encoder (CAE) model using (i) the image portions with the blacked-out center patch as an input and, (ii) the center patch as a target output and, (iii) an image-based loss function, to obtain a trained CAE model;
sampling, by the hardware processor, positive and negative center-patch-sized portions from the training images;
normalizing, by the hardware processor using the trained CAE model, the positive and negative center-patch-sized portions; and
performing, by the hardware processor, supervised training of a classifier model using the normalized positive and negative center-patch-sized portions to obtain a trained supervised classifier model for detecting the defective products;
wherein said step of sampling the positive and negative center-patch-sized portions comprises (i) avoiding invalid areas, (ii) augmenting the positive and negative patch portions by combinations of a horizontal axis flip, a vertical axis flip, and 90 degree rotations, and (iii) augmenting the positive and negative samples by combinations of free rotations and warping.

\* \* \* \* \*